(12) United States Patent
Mönkkönen et al.

(10) Patent No.: US 10,488,310 B2
(45) Date of Patent: Nov. 26, 2019

(54) APPARATUS AND METHOD FOR TENSILE TESTING

(71) Applicant: ROSENDAHL NEXTROM GMBH, Pischelsdorf (AT)

(72) Inventors: Jukka Mönkkönen, Vantaa (FI); Tomi Dahl, Pischelsdorf (AT)

(73) Assignee: ROSENDAHL NEXTROM GMBH, Pischelsdorf (AT)

( * ) Notice: Subject to any disclaimer, the term of this patent is extended or adjusted under 35 U.S.C. 154(b) by 155 days.

(21) Appl. No.: 15/694,438

(22) Filed: Sep. 1, 2017

(65) Prior Publication Data
US 2018/0067025 A1 Mar. 8, 2018

(30) Foreign Application Priority Data

Sep. 5, 2016 (FI) ...................................... 20165657

(51) Int. Cl.
*G01L 3/08* (2006.01)
*G01N 3/08* (2006.01)
*G01M 11/00* (2006.01)
*G01M 11/08* (2006.01)

(52) U.S. Cl.
CPC ............. *G01N 3/08* (2013.01); *G01M 11/088* (2013.01); *G01M 11/30* (2013.01)

(58) Field of Classification Search
None
See application file for complete search history.

(56) References Cited

U.S. PATENT DOCUMENTS 4,148,218 A * 4/1979 Knowles .............. G01M 11/088
65/486
4,601,208 A 7/1986 McKay et al.
(Continued)

FOREIGN PATENT DOCUMENTS

DE 2512993 A1 9/1976
GB 1375058 A 11/1974
(Continued)

OTHER PUBLICATIONS

Mar. 22, 2017 Search Report issued in Finnish Patent Application No. 20165657.
(Continued)

*Primary Examiner* — Peter J Macchiarolo
*Assistant Examiner* — Jermaine L Jenkins
(74) *Attorney, Agent, or Firm* — Oliff PLC

(57) ABSTRACT

The invention relates to an apparatus (1) for tensile testing of an optical fiber (11). In order to efficiently and simply test the optical fiber, the apparatus comprises a dual pulley (6) with a first circumferential surface (7) having a first diameter (D1) and with a second circumferential surface (8) having a second diameter (D2) which is larger than the first diameter (D1). A fiber inlet (10) which is delimited by the first circumferential surface (7) and the first drive belt section (2) contacts the first circumferential surface (7). A fiber outlet (13) which is delimited by the second circumferential surface (8) and the second drive belt section (3) contacts the second circumferential surface (8), and a guide (12) passes the optical fiber (11) from the fiber inlet (10) to the fiber outlet (13).

11 Claims, 3 Drawing Sheets

(56) References Cited

U.S. PATENT DOCUMENTS

| | | | | |
|---|---|---|---|---|
| 5,076,104 | A * | 12/1991 | Glaesemann | G01M 11/088 73/830 |
| 6,892,589 | B2 * | 5/2005 | Turunen | G01M 11/088 242/474.7 |
| 7,832,675 | B2 * | 11/2010 | Bumgarner | B65H 54/88 242/157.1 |
| 8,689,636 | B2 * | 4/2014 | Bednarczyk | G01M 11/088 73/800 |
| 9,574,969 | B2 * | 2/2017 | Bumgarner | G01M 11/30 |
| 9,611,124 | B2 * | 4/2017 | Yamada | B65H 63/036 |
| 10,099,888 | B2 * | 10/2018 | Seppelin | B65H 51/10 |
| 2013/0255397 | A1 | 10/2013 | Bednarczyk et al. | |

FOREIGN PATENT DOCUMENTS

| | | |
|---|---|---|
| JP | S60-189832 U | 12/1985 |
| JP | H02-229734 | 9/1990 |
| JP | H04-164227 A | 6/1992 |
| JP | 3055926 B2 | 6/2000 |
| JP | 2015137995 A | 7/2015 |
| WO | 01/71304 A2 | 9/2001 |

OTHER PUBLICATIONS

Feb. 12, 2019 Intention to Grant issued in European Patent Application No. 17 189 200.3.
Jul. 30, 2018 Office Action issued in Korean Patent Application No. 10-2017-0111550.
Aug. 10, 2018 Office Action issued in Japanese Patent Application No. 2017-168358.
Feb. 2, 2018 Search Report issued in European Patent Application No. 17189200.3.

* cited by examiner

APPARATUS AND METHOD FOR TENSILE TESTING

BACKGROUND OF THE INVENTION

Field of the Invention

This invention relates to tensile testing of an optical fiber. Such tensile testing may be routinely carried out in order to ensure that the strength of a produced optical fiber fulfills predefined requirements.

Description of Prior Art

Previously there is known a solution for tensile testing of an optical fiber where the optical fiber is pulled by a pulling device through a fiber path of the used testing apparatus. In this testing apparatus a speed difference is created between the leading end and the trailing end of the optical fiber. Due to the speed difference an internal stress or tension is created in the optical fiber. In case the optical fiber does not fulfill the requirements, the optical fiber breaks during testing.

A problem with the previously known solution is that the testing apparatus needed for carrying out tensile testing is relatively complicated, and therefore the costs caused by tensile testing are unnecessary high.

Additionally, in case the optical fiber breaks during testing, the remaining untested part of the optical fiber needs to be threaded into the fiber path before the tensile testing can continue. Such threading is a relatively slow and cumbersome manual process.

SUMMARY OF THE INVENTION

An object of the present invention is to solve the above mentioned drawbacks and to provide an efficient solution for tensile testing of an optical fiber which simplifies and speeds up the testing procedure such that the costs involved can be minimized. This is achieved with an apparatus for tensile testing according to independent claim 1 and with a method for tensile testing according to independent claim 12.

The use of a dual pulley with a first and second circumferential surface having different diameters in combination with a first drive belt section and a second drive belt section contacting the first circumferential surface, and respectively, the second circumferential surface makes it possible to obtain a simple testing procedure facilitating efficient testing of an optical fiber simultaneously as a possible break of the optical fiber during testing can be easily handled.

BRIEF DESCRIPTION OF DRAWINGS

In the following the present invention will be described in closer detail by way of example and with reference to the attached drawings, in which.

DESCRIPTION OF AT LEAST ONE EMBODIMENT

Figure 1:
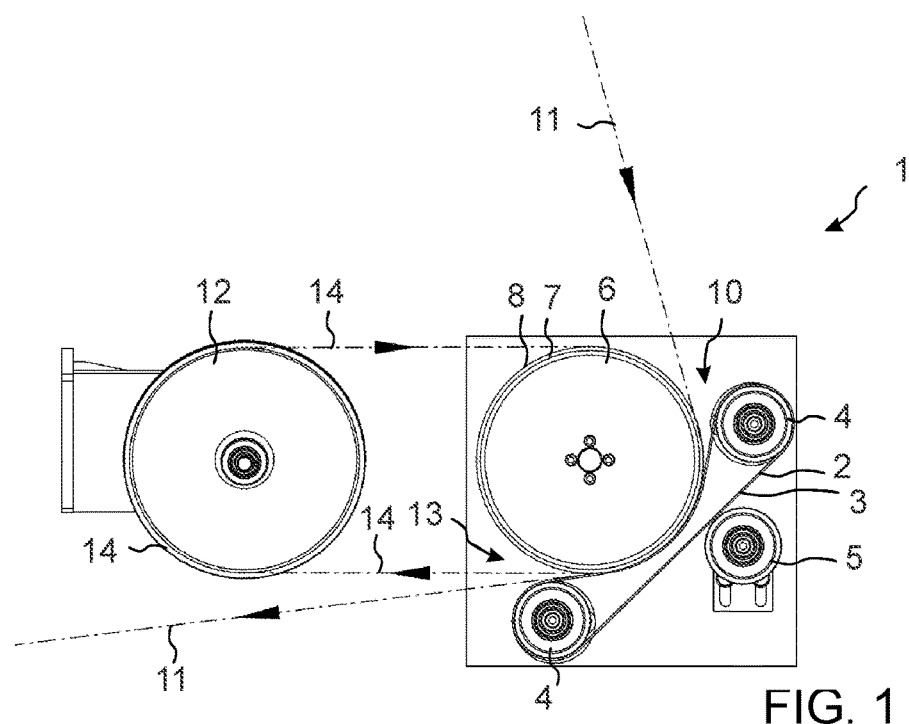
FIGS. 1 to 3 illustrate a first embodiment of tensile testing.
Figure 2:
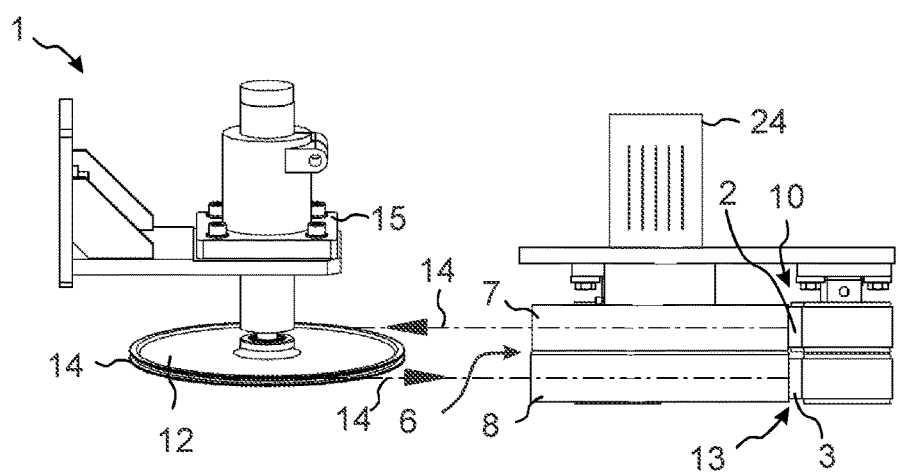
Figure 3:
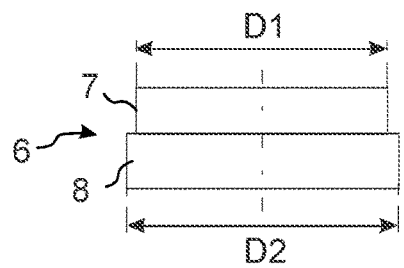

FIGS. 1 to 3 illustrate a first embodiment of a tensile testing apparatus 1 and of a method for tensile testing of an optical fiber. FIG. 1 illustrates the testing apparatus 1 from above, FIG. 2 is a top view of the testing apparatus 1 and FIG. 3 illustrates the dual pulley 6 of FIGS. 1 and 2 in more detail.

The testing apparatus 1 which is suitable for continuous testing of a practically endless optical fiber, comprises a first drive belt section 2 and a second drive belt section 3 which move side by side around belt pulleys 4. In the embodiment of FIGS. 1 to 3 it is by way of example assumed that the first drive belt section 2 and the second drive belt section 3 are drive belt sections of two different drive belts. The number of pulleys 4 may vary depending on the implementation. In the illustrated example it is by way of example assumed that each drive belt section 2 and 3 rotates around two pulleys 4. Additionally each drive belt section 2 and 3 contacts an adjustment pulley 5 which can be moved (vertically in FIG. 1) in relation to the pulleys 4 in order to adjust the tension of the drive belt or drive belts.

The apparatus 1 also comprises a dual pulley 6. In this embodiment the dual pulley 6 is implemented as one single pulley comprising a first circumferential surface 7 having a first diameter D1 and a second circumferential surface 8 having a second diameter D2. The second diameter D2 is larger than the first diameter D1. A single drive unit 24 comprising an electric motor, for instance, rotates the dual pulley 6.

The first drive belt section 2 is aligned with the first circumferential surface 7 of the dual pulley 6 and contacts the first circumferential surface 7 such that the first drive belt section 2 rotates with the dual pulley 6. The first drive belt section 2 and the first circumferential surface 7 together delimit a fiber inlet 10 into which an optical fiber 11 is received for tensile testing.

A guide 12 is arranged at a distance from the dual pulley 6. This distance is kept constant by preventing mutual movement between the guide 12 and the dual pulley 6. In the embodiment of FIGS. 1 to 3 the guide 12 comprises a freely rotating pulley around which the optical fiber 11 is passed. The freely rotating pulley of the guide 12 is aligned with the first circumferential surface 7 of the dual pulley 6 for receiving the optical fiber 11 from the fiber inlet 10 and with the second circumferential surface 8 for passing on the optical fiber 11 to a fiber outlet 13.

The second drive belt section 3 is aligned with the second circumferential surface 8 of the dual pulley 6 and contacts the second circumferential surface 8 such that the second drive belt section 3 rotates with the dual pulley 6. The second drive belt section 3 and the second circumferential surface 8 together delimit the fiber outlet 13 from where the optical fiber 11 is passed on after tensile testing.

As is apparent from the figures and the above explanation there is a difference in the diameter D1 of the first circumferential surface 7 and the diameter D2 second circumferential surface 8 (D1<D2) of the dual pulley 6. As the optical fiber is forced into contact with both of these by means of the first drive belt section 2 and the second drive belt section 3, a speed difference occurs between the fiber inlet 10 and the fiber outlet 13 when the dual pulley 6 rotates. This speed difference creates tension or internal stress in the optical fiber, which eventually may break the optical fiber in case the optical fiber 11 is not strong enough. The amount of tension obtained is dependent on the diameter difference between the first 7 and second 8 circumferential surface, and can consequently be adjusted suitable for the tested optical fiber by selecting a suitably dimensioned dual pulley.

In case the optical fiber breaks during testing, such breaking typically occurs on the section 14 of the optical fiber 11 which at that moment is located on the line pulley of the guide 12 or between the line pulley and the dual pulley 6, because during testing the tension in the optical fiber is highest in this section 14. In that case after a break, the new leading end of the optical fiber 11 remains trapped in the fiber inlet 10, where it is kept in place due to contact with the first drive belt section 2 and the first circumferential surface 7. This makes it very simple and quick for maintenance personal to grab the new leading end, to guide it via the line pulley of the guide 12 and into the fiber outlet 13 between the second drive belt section 3 and the second circumferential surface 8, after which tension testing with the apparatus 1 may again continue.

In the illustrated example the first drive belt section 2 and the second drive belt section 3 are driven by one single drive unit 24 which causes the dual pulley 6 to rotate. Such a solution makes it possible to obtain a very simple and cost efficient tensile testing apparatus, as due to only one single drive unit, the costs are minimized and a need to synchronize rotation speeds of several separate drive units, for instance, may be avoided.

An advantage obtained by using the illustrated and above explained testing solution is that efficient tensile testing starts practically immediately when the fiber 11 starts to move within the apparatus 1. This is achieved as the tensile testing does not require any particular line speed, but instead efficient tensile testing occurs already while the fiber still accelerates within the apparatus.

In some implementations a tension measurement device 15 may be arranged in connection with the freely rotating line pulley of the guide 12 in order to obtain a measurement result indicating the tension of the optical fiber during testing. A tension measurement device 15 is, however, not necessary in all embodiments, because by selecting suitable diameters D1 and D2 for the first circumferential surface and the second circumferential surface the tension in the optical fiber can be brought to a level which is sufficiently high to ensure that if the optical fiber does not break, then the optical fiber has passed the test.

Figure 4:
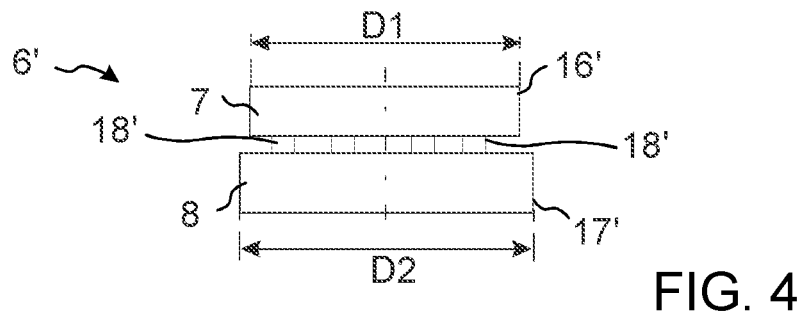
FIG. 4 illustrates an alternative dual pulley.

FIG. 4 illustrates an alternative dual pulley 6', which may be utilized in the apparatus of FIGS. 1 and 2 instead of the dual pulley 6.

Similarly as in the previous embodiment the dual pulley 6' comprises a first circumferential surface 7 having a first diameter D1 and a second circumferential surface 8 having a second diameter D2, where the second diameter D2 is larger than the first diameter D1.

In the embodiment of FIG. 4 the dual pulley is implemented as two separate coaxially arranged pulleys 16' and 17' which are attached to each other for rotating together with a same rotating speed. One alternative is that the pulleys 16' and 17' are attached to each other by bolts 18', as illustrated in FIG. 4. Alternatively the pulleys 16' and 17' may be attached on one common shaft, for instance, such that they both rotate with the same speed as the shaft.

Figure 5:
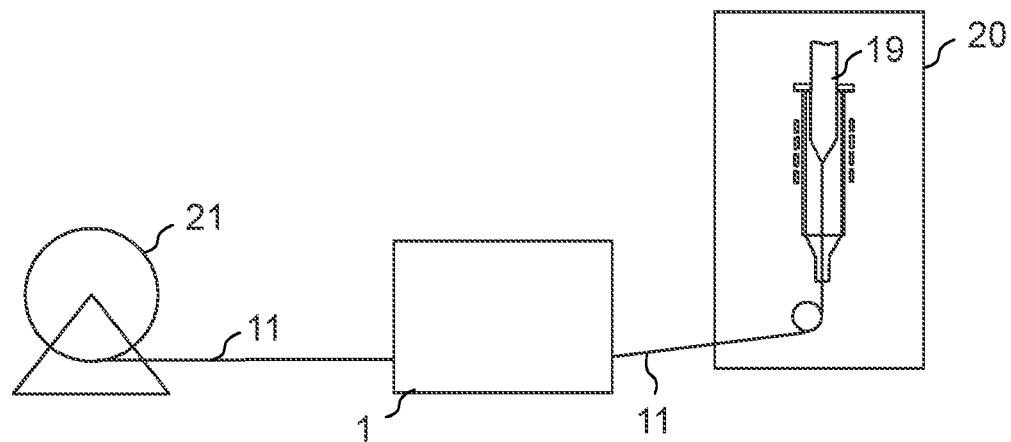
FIG. 5 illustrates in-line tensile testing.

FIG. 5 illustrates in-line tensile testing by utilizing the apparatus 1 illustrated in FIGS. 1 and 2 and with a dual pulley according to FIG. 3 or 4.

In-line testing refers in this connection to a solution where an optical fiber 11 is drawn from a glass preform 19 by a drawing device 20 and where the drawn optical fiber 11 is passed on to the tensile testing apparatus 1 without intermediate storage. Storage of the optical fiber 11 occurs after the optical fiber has passed through tensile testing apparatus 1, which passes on the optical fiber to a winding device 21.

FIG. 5 illustrates only a very simplified version of the in-line testing apparatus. In praxis other non-illustrated devices may be utilized for processing the optical fiber 11 at the drawing device 20 or at locations between the drawing device 20 and the tensile testing apparatus 1 or between the tensile testing apparatus 1 and the winding device 21.

Figure 6:
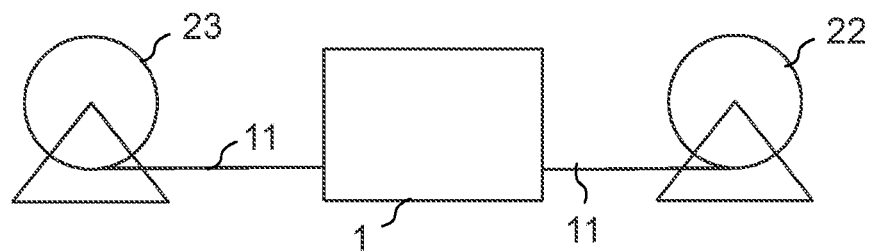
FIG. 6 illustrates off-line tensile testing.

FIG. 6 illustrates off-line tensile testing by utilizing the apparatus 1 illustrated in FIGS. 1 and 2 and with a dual pulley according to FIG. 3 or 4.

Off-line testing refers in this connection to a solution where a previously produced optical fiber 11 has been stored on a first winding device 22. During testing the optical fiber is un-winded from the first winding device 22 and passed to the tensile testing apparatus 1. The tested optical fiber 11 is subsequently passed on from the tensile testing apparatus 1 to a second winding device 23 for storage.

Figure 7:
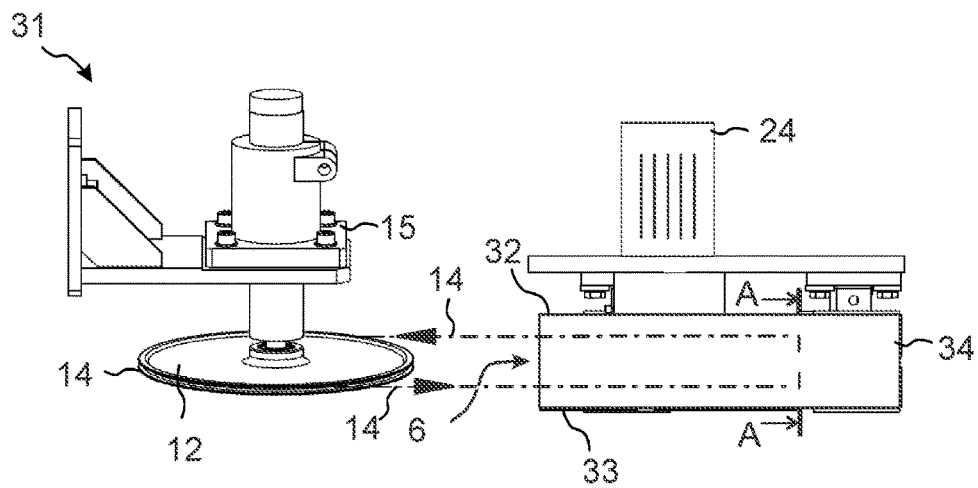
FIG. 7 illustrates a second embodiment of tensile testing.
Figure 8:
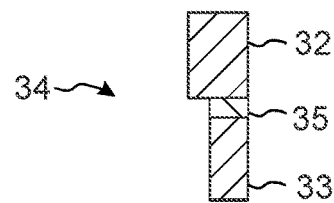
FIG. 8 illustrates a cross-section of the belt in FIG. 7.

FIGS. 7 and 8 illustrate a second embodiment of tensile testing. The embodiment illustrated in FIGS. 7 and 8 is very similar to the one explained in connection with FIGS. 1 to 3. Therefore the embodiment of FIGS. 7 and 8 will be explained mainly by pointing out the differences between these embodiments.

In the apparatus 31 illustrated in FIG. 7, the first drive belt section 32 and the second drive belt section 33 are belt sections of one single drive belt 34. One alternative to be able to implement such a solution is to utilize a drive belt 34 as illustrated in FIG. 8.

FIG. 8 illustrates a cross-section of the endless drive belt 34. Here it can be seen that the first drive belt section 32 coming into contact with the first circumferential surface 7 of the dual pulley 6 (or 6' if the dual pulley illustrated in FIG. 4 is utilized), is thicker than the second drive belt section 33 coming into contact with the second circumferential surface 8 of the dual pulley 6 (or 6'). Additionally, the first drive belt section 32 may be connected with the second drive belt section 33 via a flexible intermediate part 35 which allows temporarily mutual displacement between the first drive belt section and the second drive belt section 33. This makes it possible to compensate for the speed difference between the first and second drive belt sections 32 and 33 while they run along the first 7 and second 8 circumferential surfaces having different diameters D1 and D2.

Figure 9:
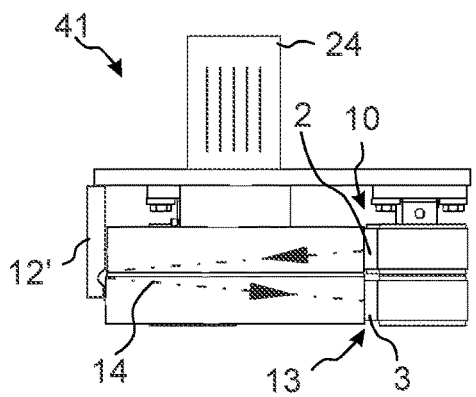
FIG. 9 illustrates a third embodiment of tensile testing.

FIG. 9 illustrates a third embodiment of tensile testing. The embodiment illustrated in FIG. 9 is very similar to the one explained in connection with FIGS. 1 to 3 and in connection with FIGS. 7 and 8. Therefore the embodiment of FIG. 9 will be explained mainly by pointing out the differences between these embodiments.

In the embodiment of FIG. 9 the guide 12' which is used in the tensile testing apparatus 41 to guide section 14 of the optical fiber from the fiber inlet 10 to the fiber outlet 13 does not have a pulley, as in the previous embodiments. Instead the guide is implemented as a non-rotating part, such as a plate with a hole at a suitable location, which contacts the optical fiber in such a way that the optical fiber is guided from the fiber inlet 10 to the fiber outlet 13.

Figure 10:
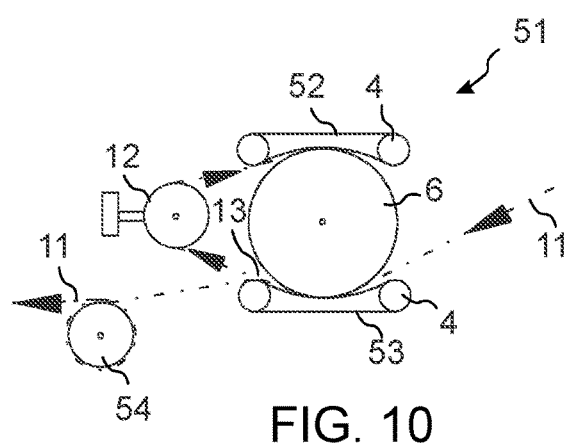
FIG. 10 illustrates a fourth embodiment of tensile testing.

FIG. 10 illustrates a fourth embodiment of tensile testing. The embodiment illustrated in FIG. 10 is very similar to the one explained in connection with FIGS. 1 to 3 and in connection with FIGS. 7 and 8. Therefore the embodiment of FIG. 10 will be explained mainly by pointing out the differences between these embodiments.

In the embodiment of FIG. 10 the first drive belt section 52 and the second drive belt section 53 in the tensile testing apparatus 51 are drive belt sections of different drive belts, and these drive belts have been arranged on opposite sides of the dual pulley 6 (or 6' if the dual pulley illustrated in FIG. 4 is utilized).

Additionally, in this example the dual pulley 6 (or 6') is freely rotating, in other words, there is no drive unit driving the dual pulley 6. Instead one single drive unit 54 is provided to pull the optical fiber 11 from the fiber outlet 13. The drive unit may be implemented as an additional pulley around which a turn of the optical fiber is wound and as an electric motor arranged to rotate this additional pulley, for instance.

It is to be understood that the above description and the accompanying figures are only intended to illustrate the present invention. It will be obvious to a person skilled in the art that the invention can be varied and modified without departing from the scope of the invention.

The invention claimed is:

1. An apparatus for tensile testing of an optical fiber, the apparatus comprising:
   a dual pulley with a first circumferential surface having a first diameter and with a second circumferential surface having a second diameter which is larger than the first diameter,
   a first drive belt section contacting the first circumferential surface of the dual pulley and a second drive belt section contacting a second circumferential surface of the dual pulley,
   a fiber inlet which is delimited by the first circumferential surface and the first drive belt section contacting the first circumferential surface,
   a fiber outlet which is delimited by the second circumferential surface and the second drive belt section contacting the second circumferential surface,
   a guide passing the optical fiber from the fiber inlet to the fiber outlet, and
   one single drive unit which rotates the first drive belt section and the second drive belt section, wherein
   the apparatus is an in-line tensile testing apparatus receiving an optical fiber from a device drawing the optical fiber from a preform and passing on the received and tensile tested optical fiber to a winding device.

2. The apparatus according to claim 1, wherein the first drive belt section and the second drive belt section are drive belt sections of one single drive belt.

3. The apparatus according to claim 1, wherein the first drive belt section and the second drive belt section are drive belt sections of two separate drive belts.

4. The apparatus according to claim 1, wherein the dual pulley is provided as one single pulley comprising the first circumferential surface and the second circumferential surface.

5. The apparatus according to claim 1, wherein the dual pulley is provided as two separate coaxially arranged pulleys arranged to rotate together.

6. The apparatus according to claim 1, wherein the first drive belt section and the second drive belt section are driven by one single drive unit which rotates the dual pulley.

7. The apparatus according to claim 1, wherein the first drive belt section and the second drive belt section are driven by one single drive unit which pulls the optical fiber from the fiber outlet.

8. The apparatus according to claim 1, wherein the guide comprises a freely rotating pulley for passing the optical fiber from the fiber inlet to the fiber outlet.

9. The apparatus according to claim 8, wherein a tension measurement device is arranged at the freely rotating pulley for measuring tension in the optical fiber.

10. An apparatus for tensile testing of an optical fiber, the apparatus comprising:
    a dual pulley with a first circumferential surface having a first diameter and with a second circumferential surface having a second diameter which is larger than the first diameter,
    a first drive belt section contacting the first circumferential surface of the dual pulley and a second drive belt section contacting a second circumferential surface of the dual pulley,
    a fiber inlet which is delimited by the first circumferential surface and the first drive belt section contacting the first circumferential surface,
    a fiber outlet which is delimited by the second circumferential surface and the second drive belt section contacting the second circumferential surface,
    a guide passing the optical fiber from the fiber inlet to the fiber outlet, and
    one single drive unit which rotates the first drive belt section and the second drive belt section, wherein
    the apparatus is an off-line tensile testing apparatus receiving an optical fiber from a first winding device and passing on the received and tensile tested optical fiber to a second winding device.

11. A method for tensile testing of an optical fiber, wherein the method comprises:
    reception of an optical fiber into a fiber inlet which is delimited by a first circumferential surface of a dual pulley and a first drive belt section contacting the first circumferential surface,
    passing on the optical fiber from the fiber inlet via a guide to a fiber outlet,
    reception of the optical fiber into the fiber outlet which is delimited by a second circumferential surface of the dual pulley having a larger diameter than the diameter of the first circumferential surface and a second drive belt section which contacts the second circumferential surface,
    rotating the first drive belt section and the second drive belt section with one single drive unit, and
    passing on the tested optical fiber from the fiber outlet.

* * * * *